United States Patent
Popov et al.

(10) Patent No.: US 7,125,723 B2
(45) Date of Patent: Oct. 24, 2006

(54) METHOD AND ASSAY KIT FOR EVALUATION OF THE OXIDATIVE MODIFICATION OF PROTEIN-CONTAINING SUBSTANCES

(76) Inventors: Igor Popov, Scharnhorststrasse 2, Berlin (DE) D10115; Gudrun Lewin, Scharnhorststrasse 2, Berlin (DE) D10115

( * ) Notice: Subject to any disclaimer, the term of this patent is extended or adjusted under 35 U.S.C. 154(b) by 242 days.

(21) Appl. No.: 10/289,346

(22) Filed: Nov. 7, 2002

(65) Prior Publication Data
US 2003/0064523 A1  Apr. 3, 2003

Related U.S. Application Data

(60) Division of application No. 09/584,712, filed on Jun. 1, 2000, which is a continuation of application No. PCT/DE99/03234, filed on Sep. 30, 1999.

(30) Foreign Application Priority Data
Oct. 1, 1998 (DE) ................................ 198 46 148

(51) Int. Cl.
*G01N 33/00* (2006.01)
(52) U.S. Cl. ................. 436/86; 436/161; 436/164; 436/169; 436/172; 210/656
(58) Field of Classification Search ............... 436/86, 436/161, 164, 169, 172; 210/656
See application file for complete search history.

(56) References Cited

U.S. PATENT DOCUMENTS 5,108,893 A  4/1992 Baret 5,395,755 A  3/1995 Thorpe et al.
6,607,919 B1 *  8/2003 Popov et al. ............... 436/86

FOREIGN PATENT DOCUMENTS

WO  WO 91/19979  12/1991

OTHER PUBLICATIONS

XP-000879291 Jeremy Twigg, et al., "Iatrogenic DNA damage induced in human spermatozoa during sperm preparation: protective significance of seminal plasma", Molecular Human Reproduction, vol. 4, No. 5, pp. 439-445, 1998.
XP-000879163 Robert E. Pacifici, et al., "Protein Degradation as an Index of Oxidative Stress", Methods in Enzymology, vol. 186, pp. 485-502, 1990.
XP-000879280 Markku Ahotupa, et al., "Simple Methods of Quantifying Oxidation Products and Antioxidant Potential of Low Density Lipoproteins", Clinical Biochemistry, vol. 29, No. 2, pp. 139-144, 1996.
Regina Santella, "DNA Damage as an Intermediate Biomarker in Intervention Studies", P.S.E.B.M., vol. 216, pp. 166-171, 1997.

(Continued)

Primary Examiner—Monique T. Cole
(74) Attorney, Agent, or Firm—Oblon, Spivak, McClelland, Maier & Neustadt, P.C.

(57) ABSTRACT

Oxidative stress in living organisms is determined in a photochemiluminescence measuring system after separation of low-molecular weight antioxidants from protein-containing test samples that were withdrawn from these organisms using an assay kit that contains a gel chromatographic column, a photosensitizer solution, a carbonate buffer solution, and a phosphate buffer solution.

18 Claims, 2 Drawing Sheets

OTHER PUBLICATIONS

Fusako Takayama, et al., "Chemiluminescence-HPLC assay of Phosphatidylcholine hydroperoxide generated by ischemia-repufusion in the liver of rats", Biochemical Pharmacology, vol. 44, No. 12, 99. 2412-2414, 1992.

Ignor N. Popov, et al., "Photochemiluminescent Detection of Antiradical Activity: II. Testing of Nonenzymic Water-Soluble Antioxidants", Free Radical Biology Medicine, vol. 17, No. 3, pp. 267-271, 1994.

Gudrun Lewin, et al., "Photochemiluminescent detection of antiradical activity: III: a simple assay of asorbate in blood plasma", J. Biochem. Biophys. Methods, vol. 28, pp. 277-282, 1994.

Igor N. Popov, et al., "Photocemiluminescent detection of antiradical activity; IV: testing of lipid-soluble antioxidants", J. Biochem. Biophys. Methods, vol. 31, pp. 1-8, 1996.

G. Lewin, et al., "Paradox of the antiradical capacity of blood plasma proteins", 1999 SFRR (Europe) Summer Meeting, Antioxidants, Adaptation, Aging, Dresden, Germany Jul. 2-5, 1999.

I. Popov, et al., "Photochemiluminescent detection of antiradical activity. VI. Antioxidant characteristics of human blood plasma, low density lipoprotein, serum albumin and amino acids during *in vitro* oxidation", LUMINESCENCE, vol. 14, pp. 169-174, 1999.

Shinichi Miyairi et al, "Determination of Metallothionein by High-Performance Liquid Chromatography with Fluorescence Detection Using an Isocratic Solvent System", Analytical Biochemistry, vol. 258, 1998, pp. 168-175.

Charles Coudray et al, "Rapid High-Performance Liquid Chromatographic Assay for Salicylic Acid in Plasma Without Solvent Extraction", Journal of Chromatographic Science, vol. 34, Apr. 1996, pp. 166-173.

L. Kritharides et al, "A Method for Defining the Stages Low-Density Lipoprotein Oxidation by the Separation of Cholesterol- and Cholesteryl Ester-Oxidation Products Using HPLC", Analytical Biochemistry, vol. 213, 1993, pp. 79-89.

Reza Mehvar et al, "Direct Injection High-Performance Liquid Chromatography of Tetrabenazine and its Metabolite in Plasma of Humans and Rats", Journal of Pharmaceutical Sciences, vol. 75, No. 10, Oct. 1986, pp. 1006-1009.

A. Favier, "Le stress oxidant: intérêt de sa mise en évidence en biologie médicale et problèmes posés par le choix d'un marqueur", Ann. Biol. Clin, vol. 55, No. 1, Jan.-Feb. 1997, pp. 6-16.

* cited by examiner

METHOD AND ASSAY KIT FOR EVALUATION OF THE OXIDATIVE MODIFICATION OF PROTEIN-CONTAINING SUBSTANCES

BACKGROUND OF THE INVENTION

1. Field of the Invention

The present invention relates to a method and assay kit for the analysis of the oxidative modification of protein-containing substances and of the oxidative stress in biological samples by measuring the antiradical properties of their protein-containing components.

2. Discussion of the Background

Oxidative stress is a common phenomenon which is implicated in the etiopathogenesis of several diseases such as atherosclerosis, cancer, acute inflammation, etc. Methods determining the concentration of species reactive with thiobarbituric acid (TBA) or of conjugated dienes have been used as routine measurements for the determination of the degree of severity of oxidative stress. Products of lipid peroxidation, for example, malondialdehyde and 4-hydroxynonenal are reactive with thiobarbituric acid.

One drawback of the known methods for the determination of oxidative stress is the lack of specificity, because several substances react with thiobarbituric acid. Another drawback is the relative insensitivity because lipid peroxidation does not immediately accompany oxidative stress. In fact, lipid peroxidation occurs only after antioxidants have been exhausted (see FAVIER, A.: Oxidative stress: value of its demonstration in medical biology and problems posed by the choice of a marker, Ann. Biol. Clin. (Paris), Vol. 55, 1997, pp. 9–16).

Proteins, unlike lipids, react immediately to oxidative stress. Different alterations, particularly in amino acids are detected in protein degradation assays (see PACIFICI, Robert E.; DAVIES, Kelvin J. A.: Protein Degradation as an Index of Oxidative Stress. In: METHODS IN ENZYMOLOGY, Vol. 186, Part B, Eds. Packer, L. and Glazer, A. N. Academic Press, Inc. 1990, pp. 485–502). These alterations include formation of characteristic products, alterations in the secondary, tertiary and quaternary structure, electric charge, folding, hydrophobicity, fragmentation, covalent inter- and intramolecular cross-linkage or increase in proteolytic sensitivity. However, determination of these parameters is very complicated, expensive, cumbersome and often non-specific, requiring methods such as radioactive or fluorescent labeling, gel electrophoresis, Western blots and immuno-precipitation.

Accordingly, there has been a need for a simplified method that allows determination of oxidative stress in organisms and the evaluation of antiradical activity of substances, particularly without the interference of low-molecular weight antioxidants, such as ascorbic acid and uric acid.

SUMMARY OF THE INVENTION

It is an objective of the present invention to devise a new method for the determination of oxidative stress in an organism. Another objective is to devise an assay kit for the measurement of oxidative stress in an organism by investigation of body fluids, for example blood plasma.

These and other objects are achieved according to the invention, the first embodiment of which includes a method for quantitative analysis of the oxidative modification of a protein-containing substance, comprising:

purifying said protein-containing substance, thereby removing a low-molecular weight antioxidant and providing a purified protein-containing substance;

generating free radicals in said purified protein-containing substance;

measuring the antiradical properties of said purified protein-containing substance in a free-radical generating measuring system.

Another embodiment of the invention includes an assay kit for the analysis of oxidative modification of protein-containing substances, comprising:

a gel chromatographic column, an aqueous photosensitizer solution and an aqueous carbonate buffer solution.

DETAILED DESCRIPTION OF THE INVENTION

Free radicals are associated with oxidative stress and can be generated by a variety of methods, i.e., physical (radiolysis, photolysis, electrolysis, etc.), physico-chemical (thermal decomposition of nitrogen compounds, photosensitized generation), chemical ($Fe^{++}/H_2O_2$ system, $KO_2$ decomposition, autoxidation of several compounds), and biochemical from individual enzymes (e.g., xanthine oxidase) to subcellular fractions (NADPH-consuming microsomes). The effect of the antioxidants can be detected by measurement of $O_2$ consumption, light absorption, electrical conductivity, fluorescence, and chemiluminescence.

Figure 1:
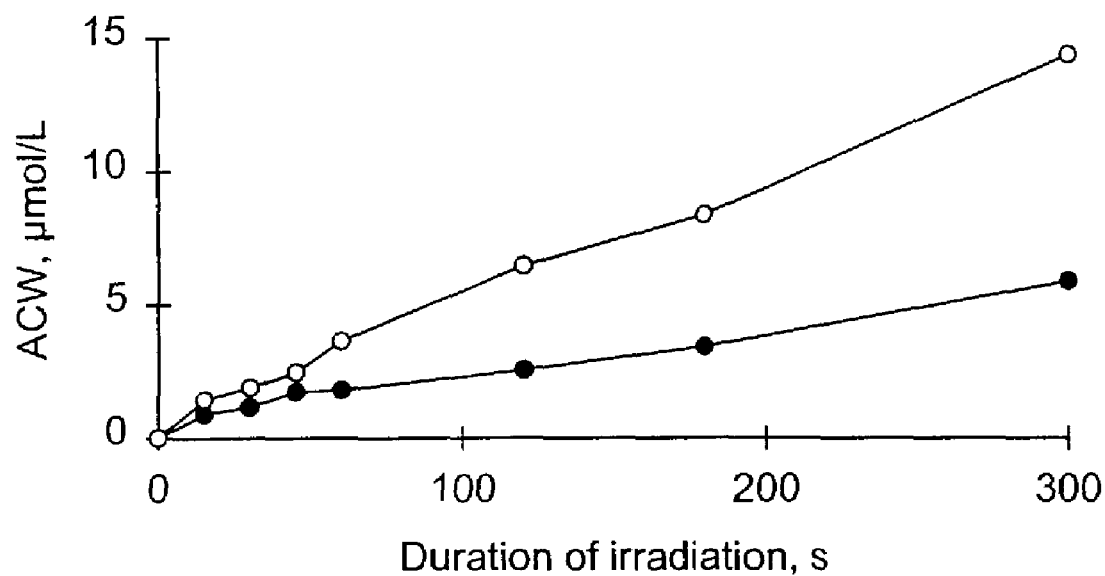
FIG. 1: Antioxidant capacity (ACW) of methionine, measured in a 2 mmol/l solution in $H_2O$ (lower curve) and human serum albumin (HSA) in a 60 g/l solution in $H_2O$ (upper curve) during irradiation with UV light ($\lambda$=254 nm) in equivalent concentration of ascorbic acid (calibration substance).
Figure 2:
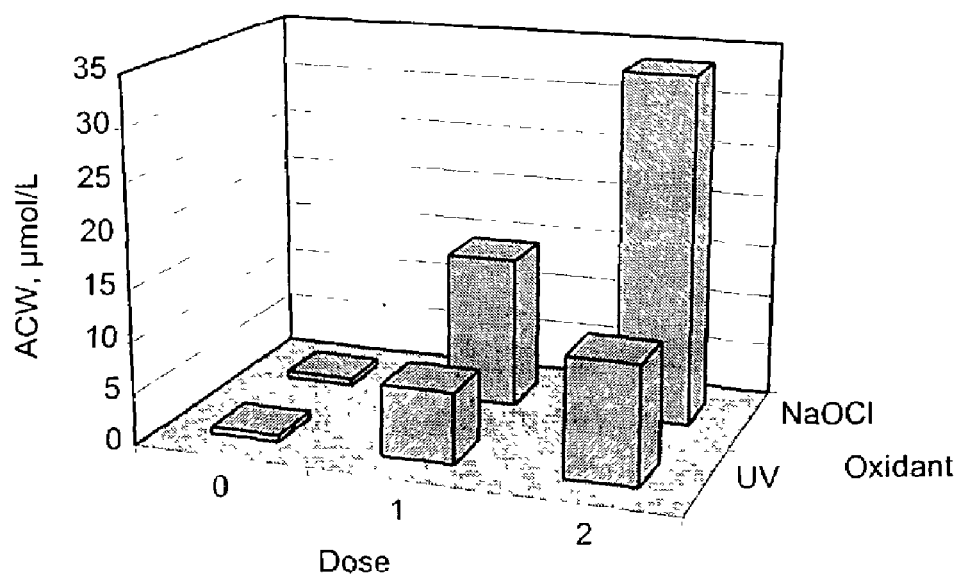
FIG. 2: Antioxidant capacity of histidine (2 mmol/l) under conditions of chemical (NaOCl) and physical (UV, $\lambda$=254 nm) oxidation in equivalent concentration of ascorbic acid (calibration substance). For UV: dose 1=60 sec, dose 2=120 sec. For NaOCl: after 45-minute incubation with 16 (dose 1) or 32 (dose 2) mg/l NaOCl.
Figure 3:
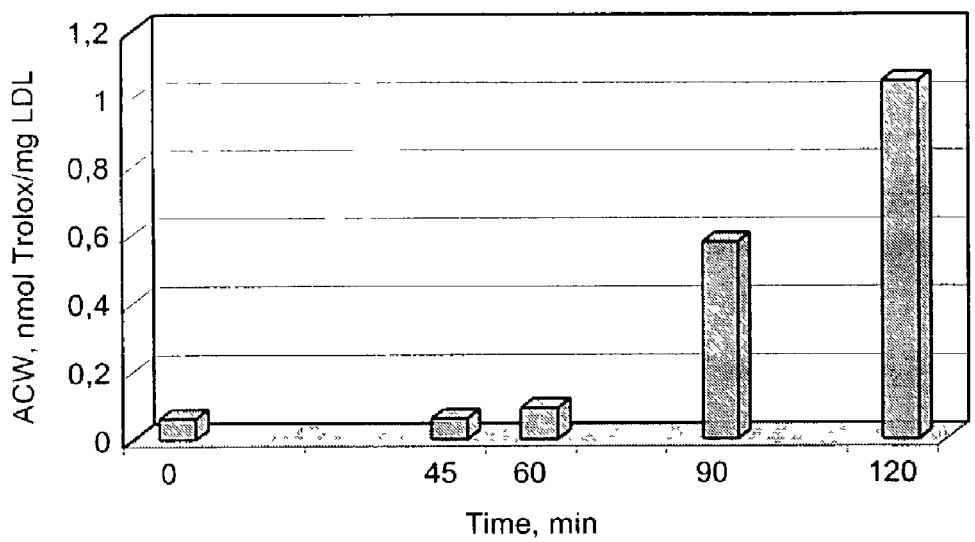
FIG. 3: Antioxidant capacity of LDL in equivalent concentration of Trolox® (calibration substance) during $Cu^{2+}$-induced oxidation.

While investigating the mechanism of the therapeutic efficacy of ultraviolet irradiation of blood, it was surprisingly found that the antioxidant capacity of blood plasma increases during UV-B irradiation, rather than, as expected, declines. An in-depth investigation of this phenomenon has revealed that this increase in antioxidant capacity can be attributed to seven amino acids (cysteine, histidine, methionine, phenylalanine, serine, tryptophan and tyrosine). Their antioxidant capacity is unfolded during irradiation and increases in accordance with the dose. The antioxidant capacity of human serum albumin (HSA) undergoes similar changes during oxidation. As shown in FIG. 1, the antioxidant capacity (ACW) of human serum albumin increases during the course of irradiation with UV-light ($\lambda$=254 nm). An increase of antioxidant capacity has also been found during irradiation of histidine solutions in which oxidative stress was induced by NaOCl or UV-light (λ=254 nm) (FIG. 2). The effects of $Cu^{2+}$-induced oxidation of LDL (low density lipoprotein) on its antioxidant capacity are shown in FIG. 3.

These so far unknown properties of blood plasma provide the basis for the determination of oxidative stress in living organisms by investigation of their protein-containing components.

The method according to the invention comprises the following steps:

A test sample is obtained from an organism, for example blood plasma or any other protein-containing substance. For example, blood is withdrawn from the cubital vein of a human. The blood plasma can be separated from the cells by, for example, centrifugation. The test sample, such as blood plasma, is then passed through a gel-chromatographic column. Such column can be a desalting column, for example, an Econo-Pac™ 10DG column from Bio-Rad which contains Bio-Gel P-6 gel. The desalted test sample is eluted from the column with a phosphate buffer saline (PBS). The phosphate buffer saline can be prepared, for example, by adding 8.18 g NaCl and 3.58 g $Na_2HPO_4 \times 12H_2O$ to 1L $H_2O$, and by adjusting the pH with HCl to 7.4.

The assay kit according to the present invention for the determination of oxidative stress in an organism by photo-chemiluminescence (PCL) investigations comprises a buffer and a photosensitizer. Preferably, the buffer has a basic pH value. More preferably the pH is between 7–14. Most preferably the pH is 10.6. The pH value includes all values therebetween, and especially including 7.5, 8.0, 8.5, 9.0, 9.5, 10.0, 10.5, 11, 11.5, 12, 12.5, 13, and 13.5. Alkali metal carbonates and earth alkali metal carbonates are preferably used as carbonates. More preferably, sodium carbonate is used as carbonate. The buffer concentrate can have a molarity of 0.1–0.3. Preferably, a 0.2 molar buffer solution in $H_2O$ is used. Different types of photosensitizer can be used, for example, riboflavine and methylene blue. Preferably, luminol is used as a photosensitizer.

The eluate from the desalting column is added to the solution comprising the buffer and the photosensitizer. The solution can also contain deionized water.

The antioxidant capacity is preferably measured in a photochemiluminescence (PCL) measuring system. Free radicals can be generated in a free-radical generating system such as a photochemiluminescence (PCL) measuring system. Such system can be a Photochem® unit consisting of a cell for irradiation, a low pressure mercury lamp, a peristaltic mini-pump, a chemiluminescence measuring cell, and a personal computer. (Popov, I., Lewin, G. Antioxidative homeostasis: characterization by means of chemiluminescent technique. In: METHODS IN ENZYMOLOGY, Vol. 300, Eds. Packer, L. and Glazer, A. N., Academic Press, New York, 1999, p.p. 437–456).

Surprisingly, it was revealed that the antiradical (antioxidant) capacity of the proteins obtained from blood plasma increases in a dose-related manner after oxidative stress caused by both chemical (e.g. hypochlorite) and physical (e.g. ultraviolet light) factors. This capacity remains unchanged for at least 24 hours after treatment. Accordingly, it is possible to quantitatively determine the degree of oxidative stress in the organism after withdrawing blood and separation of proteins.

The oxidative capacity of a substance can be evaluated according to the degree of change of a parameter of the registered curve. This is the so-called lag-phase. the longer the lag-phase, the higher the antioxidative capacity of the substance. The antioxidative capacity of different substances is compared to a standard substance (calibration substant). Preferably ascorbic acid is used as standard substance. Accordingly, the antioxidative capacity is expressed in concentration units (mmol/l) of ascorbic acid, that has the same activity (lag-phase) in the measuring system.

The calibration proceeds as follows:

Solutions of different concentrations of ascorbic acid are prepared, containing, for example, 1, 2, 3, 4, and 5 nmol of ascorbic acid. A diagram for the dependence of the lag-phase from the concentration of the acid is then prepared based on the measurement of the antioxidative capacity of ascorbic acid. The lag-phase of measured samples can then easily be correlated to a specific concentration of the ascorbic acid. Accordingly, the measuring results can be evaluated in the PCL measuring system in equivalent concentrations of a suitable calibration substance (ascorbic acid or Trolox® consisting of a water soluble derivative of alpha-tocopherol), but also in absolute terms in seconds of the lag phase, of the point of inflection (maximum value of the first derivative) or as a percentage of inhibition (with the integral as evaluation parameter) of the PCL curves.

Having generally described this invention, a further understanding can be obtained by reference to certain specific examples which are provided herein for purposes of illustration only, and are not intended to be limiting unless otherwise specified.

EXAMPLES

Example 1

0.5 ml blood plasma were eluted with a phosphate buffer solution in a desalting column manufactured by BIO-Rad. After passage of 2.5 ml of the eluent, 15 µl of the eluate from the subsequent total volume of 2 ml were measured in the PCL measuring system. The displacement of the point of inflection of the recorded curve, compared with that of the corresponding calibration curve, was used for conversion to the equivalent effectiveness of ascorbic acid. The resulting antioxidant capacity of the plasma proteins (ACP) was calculated in nmol ascorbic acid per mg protein, while taking account of the protein concentration in the sample (determined e.g. with the biuret method), and illustrated in ascorbic acid equivalents (ASA).

Definition: 1 ASA=10 pmol Asc/mg protein.

Example 2

The assay kit for 100 measurements consisted of 4 desalting columns and 6 bottles:

1 bottle with 120 ml 0.2 M sodium carbonate solution with 20 mg EDTA.

1 bottle with 200 ml deionized water.

4 black bottles with 0.75 ml luminol solution (3 mmol/l) (portions and dark coloring are required due to pronounced light sensitivity).

The entire measurement operation was performed as follows:

1 ml buffer was mixed with (1.5–x) ml water and x µl of a protein solution (for blank value, pure PBS solution) is added. x is 15 µl for the eluate. Then 25 µl of the luminol solution were injected. The mixture was transferred to the photochemiluminometer and the measurement was started.

After the measurement, the instrument was rinsed twice with deionized water.

Example 3

Human blood samples were examined according to the measuring principle described above. Blood was withdrawn from the cubital vein, using EDTA as an anticoagulant. Immediately after withdrawal, the plasma was separated from cells by means of centrifugation and frozen until the time of measurement.

Figure 4:
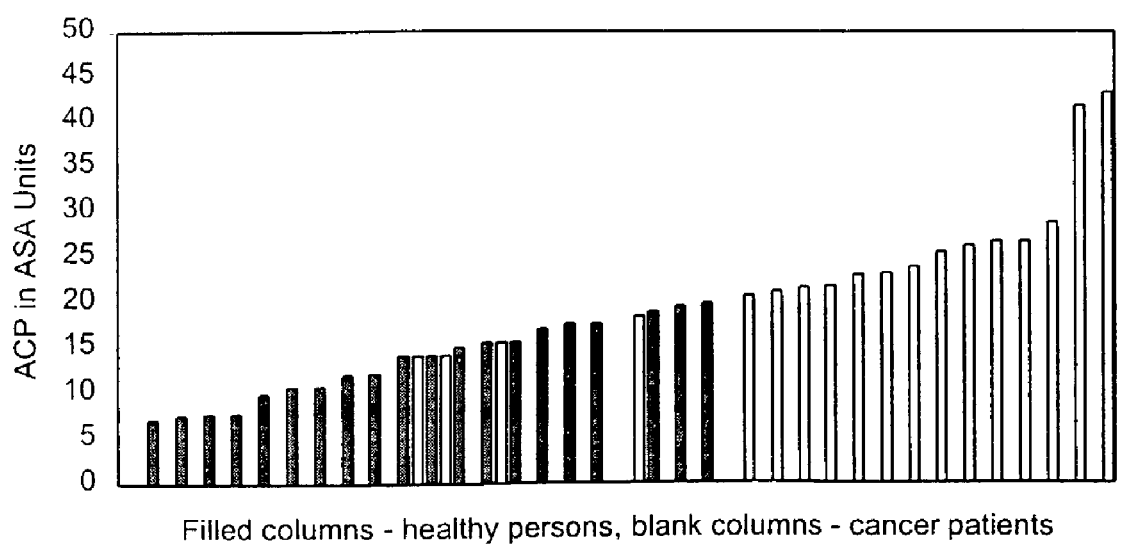
FIG. 4: Results of antioxidant capacity of plasma protein (ACP) measurements in healthy donors and cancer patients, 1 ASA=10 pmol/Asc/mg protein. Mean values: 13.5 and 21.6 ascorbic acid equivalents (ASA); error probability $p<0.0005$.

After the measurement according to Example 2 the results were evaluated on the basis of displacement of the point of inflection. Twenty healthy donors and 18 patients with breast cancer were examined. The results are shown in FIG. 4. The mean value for antioxidant capacity of plasma proteins ACP in healthy donors was 13.5 ASA and 21.6 ASA in cancer patients. The significance of the higher oxidative stress in cancer patients known from the literature was estimated according to this parameter with the error probability $p \leq 0.0005$. The error probability was determined using the T-test of an Excel-97 program. References citing data for oxidative stress in cancer include: Clin. Biochem., 1999 March, 32(2):131–6; Free Radic. Biol. Med., 1999 February; 26(3–4):410–8; J. Am. Diet. Assoc., 1998 May; 98(5): 524–8; Chem. Res. Toxicol., 1996 December; 9(8):1285–92; Cancer Epidemiol. Biomarkers Prev., 1996 September; 5(9): 705–10; Carcinogenesis, 1994 November; 15(11):2637–43; Eur. J. Clin. Nutr., 1994 August; 48(8):575–86; J. Cancer Res. Clin. Oncol. 1994; 120(6):374–7; Int. J. Epidemiol. 1992 August; 21(4):625–35; Clin. Biochem., 1999 July 32(5):369–73; Biochem. Int., 1991 September; 25(2):371–80; and J. Nutr., 1996 April 126(4 Suppl): 1201S–7S.

The priority document of the present application, German patent application, DE 198 46 148.8, filed Oct. 1, 1998 and PCT application, PCT/DE99/03234, filed Sep. 30, 1999, are incorporated herein by reference.

Obviously, numerous modifications and variations on the present invention are possible in light of the above teachings. It is therefore to be understood that within the scope of the appended claims, the invention may be practiced otherwise than as specifically described herein.

What is claimed is:

1. A method for quantitative analysis of the oxidative modification of a protein-comprising substance, comprising:
   purifying said protein-comprising substance, thereby removing a low-molecular weight antioxidant and providing a purified protein-comprising substance;
   measuring the antiradical properties of said purified protein-comprising substance in a free-radical generating system;
   comparing the measured properties with a calibration curve of a calibration substance at a given concentration; and
   expressing the antiradical capacity of said purified protein-comprising substance as concentration units of said calibration substance.

2. The method according to claim 1, wherein said protein-comprising substance is selected from the group consisting of blood plasma, tissue homogenates and cell lysates.

3. The method according to claim 1, wherein said purifying occurs in a gel-chromatographic column.

4. The method according to claim 1, wherein said purifying occurs in a desalting column.

5. The method according to claim 1, wherein said low-molecular weight antioxidant is ascorbic acid or uric acid.

6. The method according to claim 1, wherein said generating of free radicals occurs by radiolysis, photolysis, electrolysis, thermal decomposition or photosensitized generation.

7. The method according to claim 1, wherein said generating of said free radicals occurs in a $Fe^{2+}/H_2O_2$ system, by a $KO_2$ decomposition or by an enzymic reaction of an oxidase.

8. The method according to claim 1, wherein said generating of said free radicals occurs by UV-radiation.

9. The method according to claim 1, wherein said free-radical generating measuring system comprises a cell for irradiation, a low pressure mercury lamp, a peristaltic mini-pump, a chemiluminescence measuring cell, and a computer.

10. The method according to claim 1, wherein said free-radical generating system is a photochemiluminescence measuring system.

11. The method of claim 1, wherein said calibration substance is ascorbic acid.

12. The method of claim 1, wherein said purified protein-comprising substance comprises methionine.

13. The method of claim 1, wherein said purified protein-comprising substance comprises histidine.

14. The method of claim 1, wherein said purified protein-comprising substance comprises tryptophan.

15. The method of claim 1, wherein said purified protein-comprising substance comprises tyrosine.

16. The method of claim 1, wherein said purified protein-comprising substance comprises serine.

17. The method of claim 1, wherein said purified protein-comprising substance comprises phenylalanine.

18. The method of claim 1, wherein said protein-comprising substance comprises cysteine.

* * * * *